United States Patent [19]

Scaccia et al.

[11] Patent Number: 4,499,029
[45] Date of Patent: Feb. 12, 1985

[54] ISOBUTYRYL FLUORIDE MANUFACTURE
[75] Inventors: Carlo Scaccia, Worthington; John R. Overley, Westerville, both of Ohio
[73] Assignee: Ashland Oil, Inc., Ashland, Ky.
[21] Appl. No.: 504,702
[22] Filed: Jun. 15, 1983
[51] Int. Cl.³ .............................................. C07C 51/58
[52] U.S. Cl. ................................................. 260/544 A
[58] Field of Search .................................... 260/544 A
[56] References Cited
U.S. PATENT DOCUMENTS
2,831,877 4/1958 Koch ........................... 260/413 HC
4,303,594 12/1981 Norton et al. .................. 260/544 A Primary Examiner—Natalie Trousof
Assistant Examiner—L. Hendriksen
Attorney, Agent, or Firm—John F. Jones

[57] ABSTRACT

A process is described for preparing isobutyryl fluoride which involves reacting propylene, carbon monoxide and hydrogen fluoride under substantially anhydrous conditions in at least two continuous flow reaction zones, and the incremental addition of propylene and carbon monoxide to the reaction mixture at a point or points between the reaction zones.

5 Claims, No Drawings

ISOBUTYRYL FLUORIDE MANUFACTURE

This invention relates to the manufacture of isobutyryl flouride and more particularly pertains to a continuous process for the production of isobutyryl fluoride by the reaction of propylene, carbon monoxide and hydrogen fluoride.

A process for the production of carboxylic acids from olefins is disclosed in U.S. Pat. No. 2,831,877 wherein isobutyric acid is prepared by the reaction of propylene, carbon monoxide, hydrogen fluoride, and water at elevated pressure in a batch process.

The present invention which relates to the production of isobutyryl fluoride is highly advantageous over the prior art processes for production of isobutyric acid or esters in that the former proceeds at a rapid rate and produces high yields (90% or greater) of the desired isobutyryl fluoride with a desirably low ratio of hydrogen fluoride to isobutyryl fluoride at the reactor outlet.

We have discovered that the reaction of propylene, carbon monoxide and hydrogen fluoride can be carried out under substantially anhydrous conditions continuously to produce high yields of isobutyryl fluoride in a relatively short period of time by conducting the reaction in a continuous flow of the reactants in more than one reaction zone, wherein additional carbon monoxide and propylene are added to the reaction mixture at a point or points between said reaction zones. Our process can be carried out at pressures varying between atmospheric and 2200 p.s.i.a. and preferably between 300 and 1000 p.s.i.a. The process of our invention can be carried out at temperatures in the range of from 0° C. to 100° C. and preferably between about 25° C. and 60° C. The total reaction time, or average residence time of the reaction mixture in the reactor, for converting 90% or more of the propylene fed in our process to isobutyryl fluoride can vary from 15 seconds to 10 minutes and usually from 30 seconds to 3 minutes.

The molar ratio of propylene:carbon monoxide:hydrogen fluoride used as feed in our process can vary from 1:5:5 to 1:30:200, and more preferably from 1:7:15 to 1:20:100.

Our process can be carried out in any continuous flow type of reactor which has at least two reaction zones which communicate and which have means between them for the introduction of additional portions of carbon monoxide and propylene. Thus, our process involves the addition of hydrogen fluoride, propylene and carbon monoxide to the first reaction zone with further additions of carbon monoxide and propylene only into the second and succeeding reaction zones. One type of reactor which can be used in the process of this invention is a pipe reactor having two or more tubular reaction zones within it, which zones communicate with one another and have means between them for the introduction of additional reactants into the direction of flow of the reaction mixture.

The reaction mixture produced by the process of our invention can be worked up by means known to those skilled in the art to isolate the desired isobutyryl fluoride in essentially pure form and to recycle unreacted carbon monoxide, propylene and hydrogen fluoride if so desired.

Isobutyryl fluoride is readily converted to isobutyric acid by aqueous hydrolysis or it can be converted to an isobutyric acid ester by reaction with an alcohol as is well known in the art of hydrolysis or alcoholysis of acyl halides. Isobutyric acid and its esters have known uses, per se, and they can also be converted to methacrylic acid and methacrylic esters by oxydehydrogenation over a heterogeneous catalyst if desired as is also well known to those skilled in the art.

EXAMPLE

A. The reactor was a tubular reactor of about $\frac{1}{8}''$ diameter and approximately 500 feet long. About midway along the reactor tube was an inlet for admitting additional feed to the reaction mixture, thus creating two reaction zones. The mixtures of HF/propylene/CO in which the CO/propylene molar ratio was about 13 and the HF/propylene molar/ratio was slightly over 40 was fed into one end of the reactor and was pumped continuously through the reactor at 525 p.s.i.g. at room temperature. A mixture of CO/propylene was introduced continuously into the inlet of the reactor at the midpoint. The reaction time was about 1-2 minutes. Analysis of the effluent from the reactor outlet at the end of the second reaction zone showed that the overall molar yield of isobutyryl fluoride (based on propylene fed) was 90%.

B. In an experiment which is outside the scope of this invention, the reactor described in "A" of this Example was used, the same reaction conditions given in "A" were employed and all of the CO/propylene/HF was added at the same time to the reactor and nothing was added to the midpoint inlet so that the reaction was a single stage reaction. Analysis of the reactor effluent showed that the overall yield of isobutyryl fluoride (based on propylene fed) was 78%.

I claim:

1. The process for preparing isobutyryl fluoride consisting essentially of passing a substantially anhydrous reaction mixture of propylene, carbon monoxide and hydrogen fluoride through at least two continuous flow reaction zones and adding incremental amounts of substantially anhydrous propylene and carbon monoxide to the reaction mixture between reaction zones said process being carried out with a residence time in the reaction zones of from 15 seconds to 10 minutes, at a reaction pressure in the range of from atmospheric to 2200 p.s.i.a. at a reaction temperature in the range of from 0° C. to 100° C. with the molar ratio of propylene:carbon monoxide:hydrogen fluoride in the reaction mixture falling in the range of from 1:5:5 to 1:30:200.

2. The process of claim 1 carried out at a pressure in the range of from 300 to 1000 p.s.i.a.

3. The process of claim 2 carried out at a temperature in the range of from 25° C. to 60° C.

4. The process of claim 3 wherein the molar ratio of propylene:carbon monoxide:hydrogen fluoride falls in the range of from 1:7:15 to 1:20:100.

5. The process of claim 4 wherein the residence time in the reactor of the reaction mixture can vary from 30 seconds to 3 minutes.

* * * * *